(12) United States Patent
Arnin et al.

(10) Patent No.: US 7,811,323 B2
(45) Date of Patent: Oct. 12, 2010

(54) SPINAL PROSTHESES

(75) Inventors: Uri Arnin, Kiryat Tivon (IL); Michael Tauber, Tel Aviv (IL); Yuri Sudin, Lod (IL); Yoram Anekstein, Tel Aviv (IL)

(73) Assignee: Impliant Ltd., Ramat Poleg, Netanya (IL)

( * ) Notice: Subject to any disclaimer, the term of this patent is extended or adjusted under 35 U.S.C. 154(b) by 855 days.

(21) Appl. No.: 11/692,202

(22) Filed: Mar. 28, 2007

(65) Prior Publication Data

US 2007/0203494 A1 Aug. 30, 2007

Related U.S. Application Data

(63) Continuation of application No. 11/369,816, filed on Mar. 8, 2006, now Pat. No. 7,537,613, which is a continuation of application No. 10/750,860, filed on Jan. 5, 2004, now Pat. No. 7,011,685.

(60) Provisional application No. 60/517,888, filed on Nov. 7, 2003.

(51) Int. Cl.
*A61F 2/44* (2006.01)
(52) U.S. Cl. .................................. 623/17.11; 623/17.14
(58) Field of Classification Search ... 623/17.11–17.16, 623/18.11; 606/250, 246, 248, 257
See application file for complete search history.

(56) References Cited

U.S. PATENT DOCUMENTS

| 6,733,532 | B1 * | 5/2004 | Gauchet et al. | 623/17.12 |
|---|---|---|---|---|
| 7,276,082 | B2 * | 10/2007 | Zdeblick et al. | 623/17.15 |
| 7,494,507 | B2 * | 2/2009 | Dixon et al. | 623/17.14 |
| 7,566,346 | B2 * | 7/2009 | Kirschman | 623/17.14 |

* cited by examiner

*Primary Examiner*—Pedro Philogene
(74) *Attorney, Agent, or Firm*—Dekel Patent Ltd.; David Klein

(57) ABSTRACT

An article including a spinal prosthesis having a unitary body with at least three attachment points attachable to spinal structure, the unitary body including a flexure assembly positioned between first and second attachment members, wherein flexure of the flexure assembly permits movement of the first attachment member relative to the second attachment member.

2 Claims, 9 Drawing Sheets

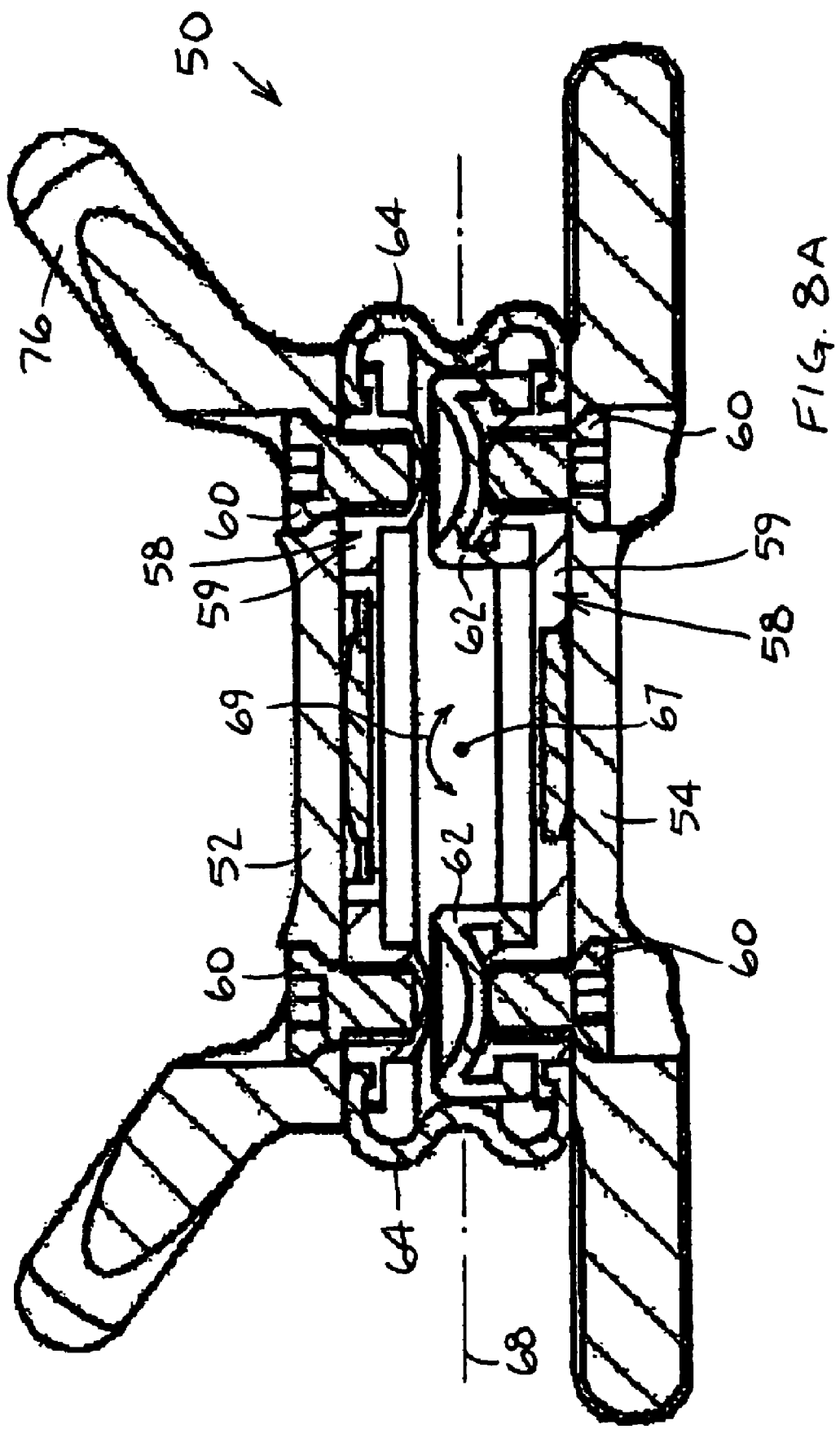

SPINAL PROSTHESES

CROSS-REFERENCE TO RELATED APPLICATIONS

This application claims priority under 35 USC §119 to U.S. Provisional Patent Application Ser. No. 60/517,888, filed Nov. 7, 2003, and is a continuation of U.S. patent application Ser. No. 11/369,816, filed Mar. 8, 2006, now U.S. Pat. No. 7,537,613, which is a continuation of U.S. patent application Ser. No. 10/750,860, filed Jan. 5, 2004, now U.S. Pat. No. 7,011,685, which are incorporated herein by reference.

FIELD OF THE INVENTION

The present invention is generally related to apparatus and methods for spinal prostheses.

BACKGROUND OF THE INVENTION

Spinal stenosis, as well as spondylosis, spondylolisthesis, osteoarthritis and other degenerative phenomena may cause back pain, especially lower back pain. Such phenomena may be caused by a narrowing of the spinal canal by a variety of causes that result in the pinching of the spinal cord and/or nerves in the spine. Fusion of two or more adjacent vertebrae has been to alleviate back pain. However, fusion of vertebrae can be disfavored because fusion tends to cause degenerative phenomena in the fused vertebrae to migrate to adjacent vertebral components that have not been fused.

SUMMARY OF THE INVENTION

The present invention seeks to provide a novel spinal prosthesis, as is described more in detail hereinbelow. The prostheses disclosed herein are particularly advantageous for the posterior portion of the spine, but the invention is not limited to the posterior portion of the spine.

There is thus provided in accordance with an embodiment of the present invention an article including a spinal prosthesis having a unitary body with at least three attachment points attachable to spinal structure, the unitary body including a flexure assembly positioned between first and second attachment members, wherein flexure of the flexure assembly permits movement of the first attachment member relative to the second attachment member.

The spinal prosthesis can include one or more of the following features. For example, the first and second attachment members may be formed with mounting holes adapted for a mechanical fastener to pass through and into the spinal structure. The first and second attachment members may include sidewalls separated by a gap, the gap being adapted for receiving therein a posterior portion of the spine. The flexure assembly may be attached to the first and second attachment members by means of a tenon-and-mortise joint. The first and second attachment members may include at least one pair of opposing resilient pawls adapted for gripping the portion of the spine. The flexure assembly may include more than one flexure member between the first and second attachment members. At least a portion of the flexure assembly may be attached to the first and second attachment members with a plurality of locking members. Alternatively, at least a portion of the flexure assembly may be integrally formed with the first and second attachment members. The locking members may include plate-like elements secured to the first and second attachment members with mechanical fasteners. The locking members may include at least one lug extending generally perpendicularly from the plate-like elements, around which at least one stopper is engaged. The flexure assembly may include a boot placed at least partially around inner portions of the first and second attachment members, the boot being connected to the first and second attachment members. The boot may be elastomeric. The flexure assembly may be adapted to flex omnidirectionally. A plurality of pedicle screws may be attached to or integrally formed with the spinal prosthesis. The pedicle screws may include polyaxial pedicle screws having a threaded shank and a polyaxial swivel head. The threaded shank and/or the polyaxial swivel head may be attached to or integrally formed with the spinal prosthesis. The first and second attachment members may include mounting arms rotatably mounted in a housing, one portion of each mounting arm being disposed in a hollow chamber formed in the housing, and another portion of each mounting arm protruding from the housing through an aperture formed in the housing. The flexure assembly may include a multi-part articulating assembly, including a first joint member that has a convex contour that articulates with a second joint member that has a concave contour that corresponds to and glides over the convex contour of the first joint member, the first and second joint members being attached to or integrally part of the attachment members. A stopper may be provided that limits the flexure of the flexure assembly and limits relative movement of the attachment members with respect to one another.

BRIEF DESCRIPTION OF THE DRAWINGS

In the drawings:

FIGS. 8A and 8B are simplified sectional illustrations, respectively along front and side facing planes, of the elastomeric spinal prosthesis shown in FIGS. 7A and 7B.

DETAILED DESCRIPTION OF EMBODIMENTS

Figure 1A:
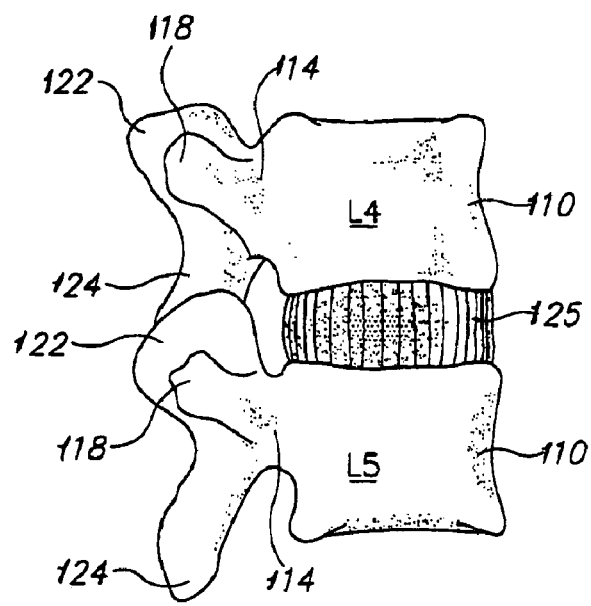
FIGS. 1A and 1B are simplified pictorial illustrations of a structure of a human spine, in particular the lumbar vertebrae, FIGS. 1A and 1B respectively showing side and top views of the L4 and L5 vertebrae.
Figure 1B:
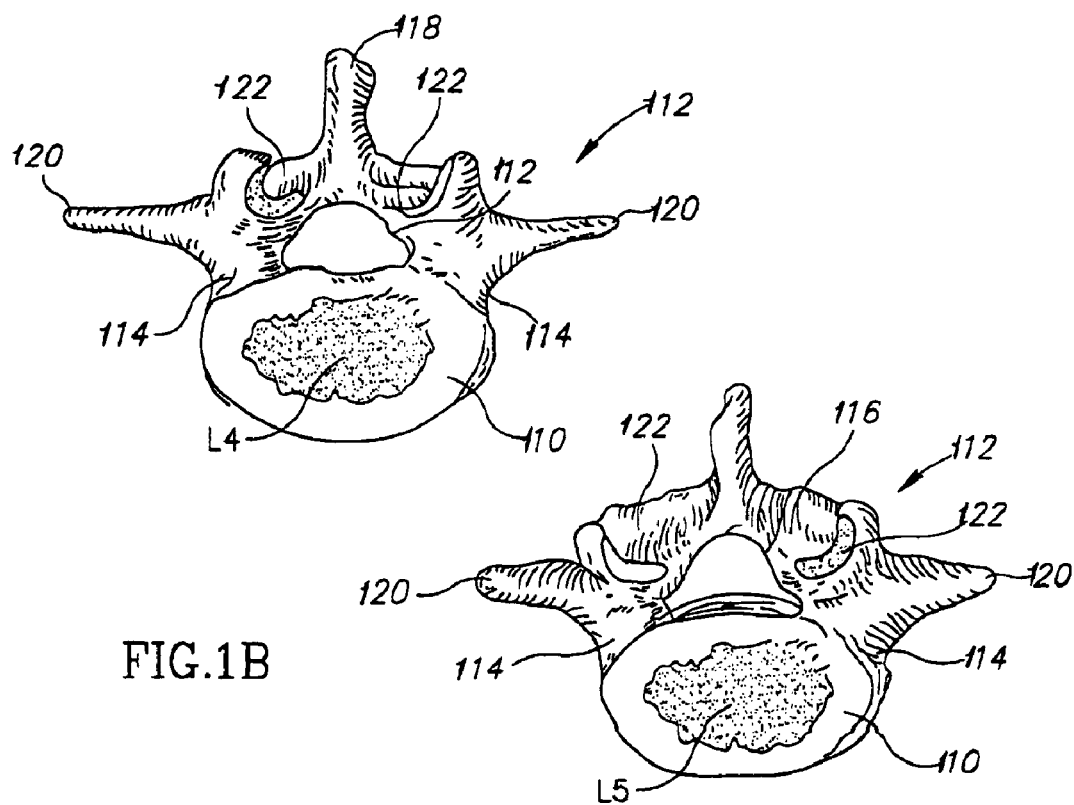

Reference is now made to FIGS. 1A and 1B, which illustrate a structure of a human spine, in particular the lumbar vertebrae.

FIGS. 1A and 1B illustrate the fourth and fifth lumbar vertebrae L4 and L5, respectively, in a lateral view (while in anatomic association) and in a superior view (separately). The lumbar vertebrae (of which there are a total of five) are in the lower back, also called the "small of the back."

As is typical with vertebrae, the vertebrae L4 and L5 are separated by an intervertebral disk 125. The configuration of the vertebrae L4 and L5 differ somewhat, but each vertebra includes a vertebral body 110, which is the anterior, massive part of bone that gives strength to the vertebral column and supports body weight. A vertebral arch 112 is posterior to the vertebral body 110 and is formed by right and left pedicles 114 and lamina 116. The pedicles 114 are short, stout processes that join the vertebral arch 112 to the vertebral body 110. The pedicles 114 project posteriorly to meet two broad flat plates of bone, called the lamina 116.

Seven other processes arise from the vertebral arch 112. A spinous process 118 and two transverse processes 120 project from the vertebral arch 112 and afford attachments for muscles, thus forming levers that help the muscles move the vertebrae. Two superior articular processes 122 project superiorly from the vertebral arch 112 and two inferior articular processes 124 project inferiorly from the vertebral arch 112. The superior articular processes 122 of a vertebra are located opposite corresponding inferior articular processes 124 of an adjacent vertebra. Similarly, inferior articular processes 124 are located opposite corresponding superior articular processes 122 of an adjacent vertebra. The intersection of a vertebra's superior articular processes 122 with the inferior articular processes 124 of an adjacent vertebra form a joint, called a zygapophysial joint, or in short hand, a facet joint or facet 126. Facet joints 126 found between adjacent superior articular processes 122 and inferior articular processes 124 along the spinal column permit gliding movement between the vertebrae L4 and L5.

Figure 1C:
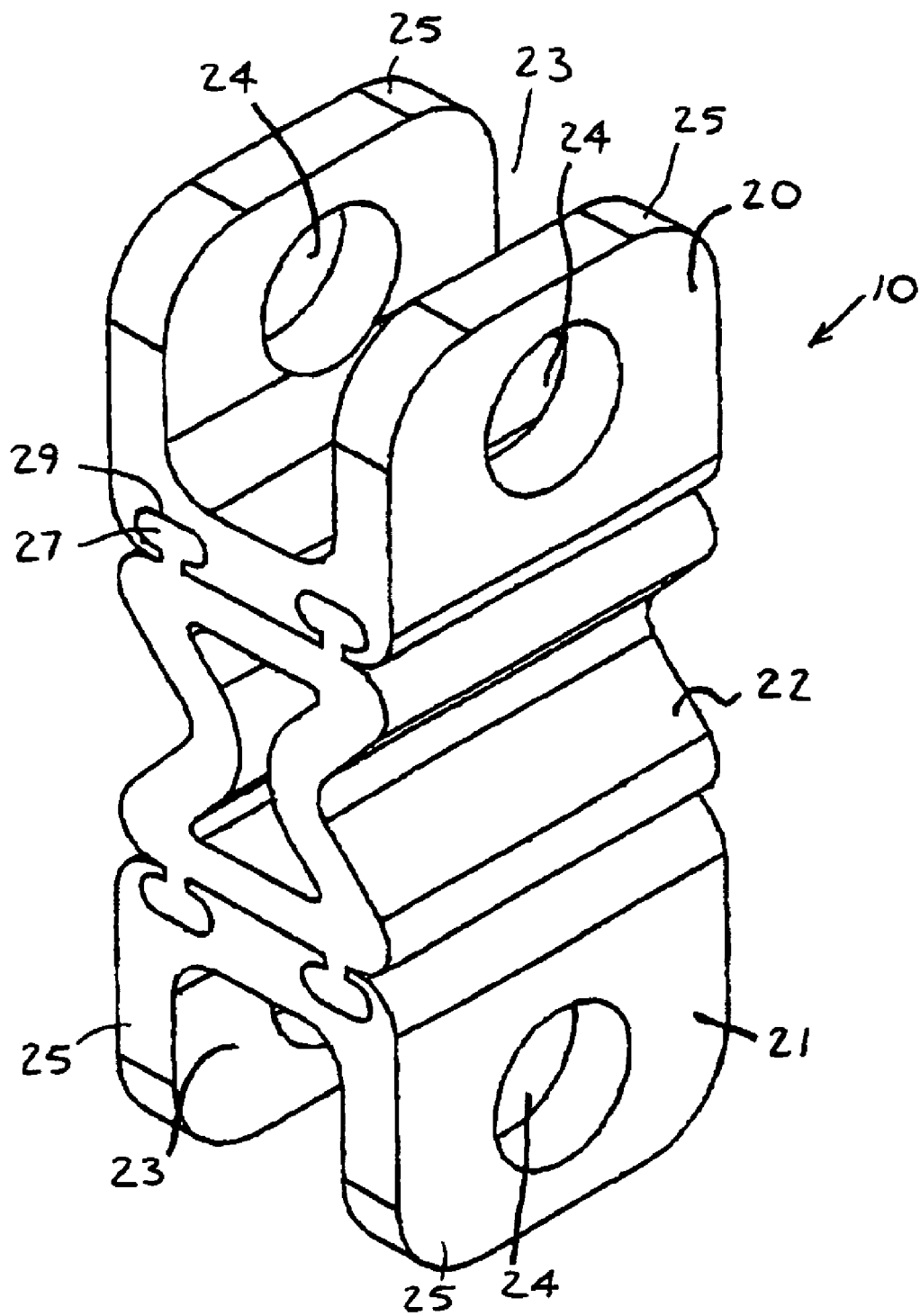
FIG. 1C is a simplified perspective illustration of an elastomeric spinal prosthesis, constructed and operative in accordance with an embodiment of the present invention.

Reference is now made to FIG. 1C, which illustrates a spinal prosthesis 10, constructed and operative in accordance with an embodiment of the present invention.

Prosthesis 10 may include an upper (superior) vertebral attachment member 20 attachable to one of the spinous processes 118 (not shown in FIG. 1C), and a lower (inferior) vertebral attachment member 21 attachable to an adjacent spinous process 118. Attachment members 20 and 21 may be rigid or non-rigid, formed of materials including, but not limited to, a biocompatible material such as a metal, e.g., stainless steel, titanium or titanium alloy, cobalt chromium alloys, plastics or other hard, rigid materials or any combination of the above.

An elastomeric member 22 (also referred to as a flexure assembly) is placed between and may be integrally formed with or attached to upper and lower vertebral attachment members 20 and 21. Elastomeric member 22 may be made from a compliant material including, but not limited to, polyurethane containing materials, silicone containing materials, polyethylene based elastomers, hydrogels, and polypropylene containing materials. Elastomeric member 22 may flex in any direction, which may help reduce tension between the attachment members 20 and 21 during movement of the spine. The flexure of elastomeric member 22 permits the attachment members 20 and 21 to move relative to one another. This may help install the prosthesis in the body by overcoming misalignments between the parts of the prosthesis and the mounting holes in the body.

In order to install prosthesis 10, any material or body structure such as ligaments may be removed or moved to the side temporarily in order to expose adjacent spinous processes. For example, a laminactomy (cutting into the lamina 116 and removing at least a portion thereof) may be performed through a posterior incision. Afterwards, the attachment members 20 and 21 may be attached to the exposed spinous processes 118 of the adjacent vertebrae.

In the embodiment of FIG. 1C, but not necessarily, upper and lower vertebral attachment members 20 and 21 are formed with mounting holes 24 adapted for a mechanical fastener (not shown) to pass through and into the spinous processes 118. For example, any fastener or fasteners, such as but not limited to, screws, bolts, rivets, nails, tacks and nuts may pass through holes 24 to firmly attach attachment members 20 and 21 to the spinous process 118.

The vertebral attachment members 20 and 21 may have sidewalls 25 separated by a gap 23 (forming a U-shape). The spinous process 118 or any posterior portion of the spine, for example, may be received snugly (or loosely) in gap 23 prior to fastening with the mechanical fastener. A hole, or holes, may be drilled into or right through the spinous process 118 at a place opposite holes 24 in order to use the mechanical fasteners to firmly attach the attachment members 20 and 21 to the spinous processes 118.

In the embodiment of FIG. 1C, but not necessarily, elastomeric member 22 may be attached to or integrally formed with upper and lower vertebral attachment members 20 and 21 by means of a tenon-and-mortise joint. The tenon-and-mortise joint may comprise tenons 27 (protrusions) that mate with mortises (grooves) 29. However, the invention is not limited to this type of joint or connection, and other types of joints, connections, fastenings, adhesive bonding and the like may also be used.

Figure 2:
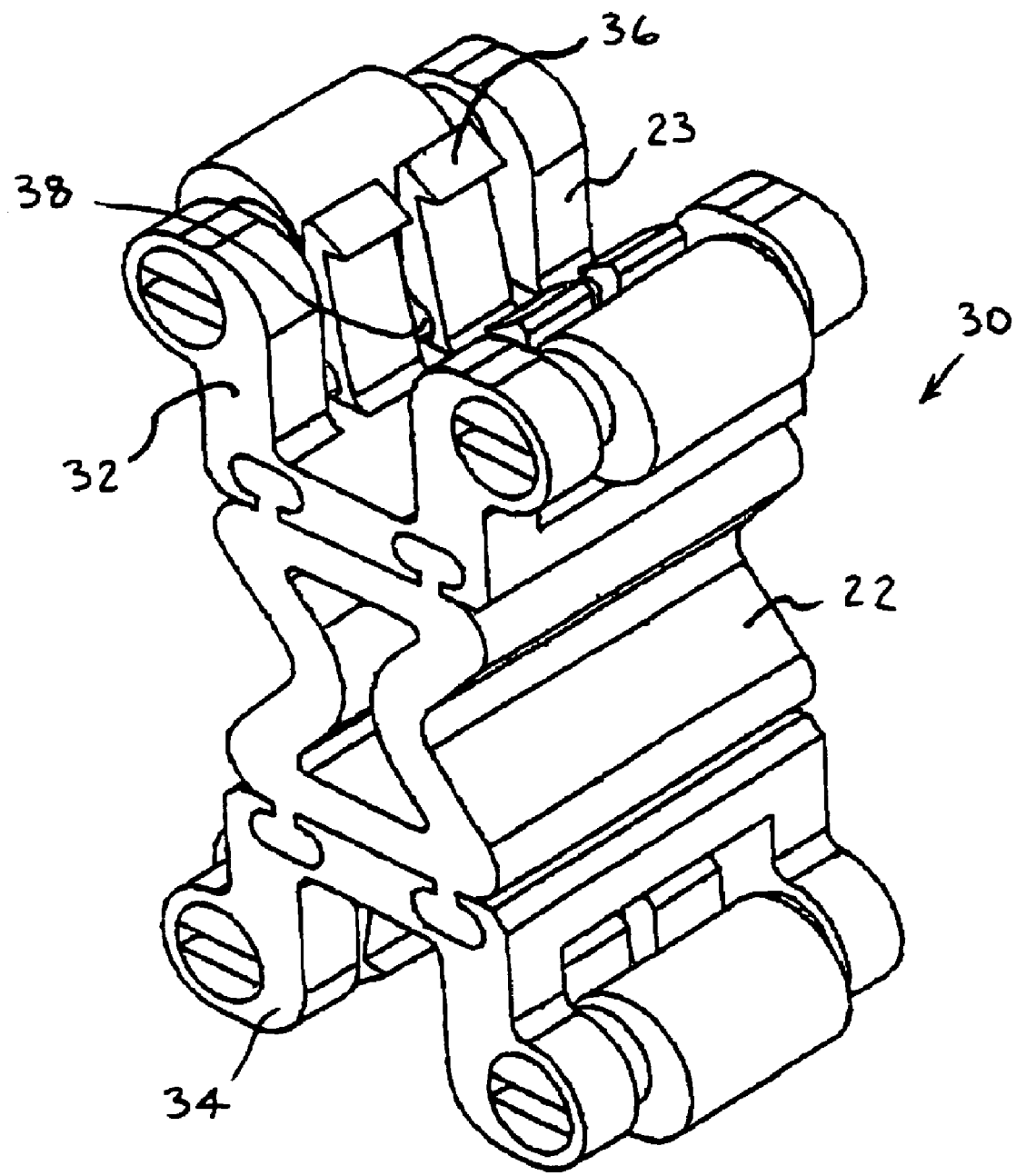
FIG. 2 is a simplified perspective illustration of an elastomeric spinal prosthesis, constructed and operative in accordance with another embodiment of the present invention.

Reference is now made to FIG. 2, which illustrates a spinal prosthesis 30 having upper and lower vertebral attachment members 32 and 34 that can be attached to a spinous process 118 without having to drill into or through the spinous process. Thus, a smaller incision to install the prosthesis 30 may be used than to install the prosthesis 10.

This embodiment may include upper and lower vertebral attachment members 32 and 34 that have one or more pairs of opposing resilient pawls 36 mounted on a base 38 and adapted for gripping the spinous process 118. The pawls 36 apply a spring force to tightly grip the spinous process 118. The attachment members may thus be pushed into place and tightly "snap on" the spinous process 118. (The spinous process 118 is received in gap 23 as before.)

In the above-described embodiments, the prosthesis may be attached to the spinous process 118 alone. However, the attachment members may be additionally or alternatively attached to other parts of the vertebra, such as but not limited to parts of the facet 126 and/or to the pedicles 114 or any posterior portion of the spine, not just the spinous process 118. Other embodiments that attach to the pedicles 114 are described further hereinbelow.

Figure 3:
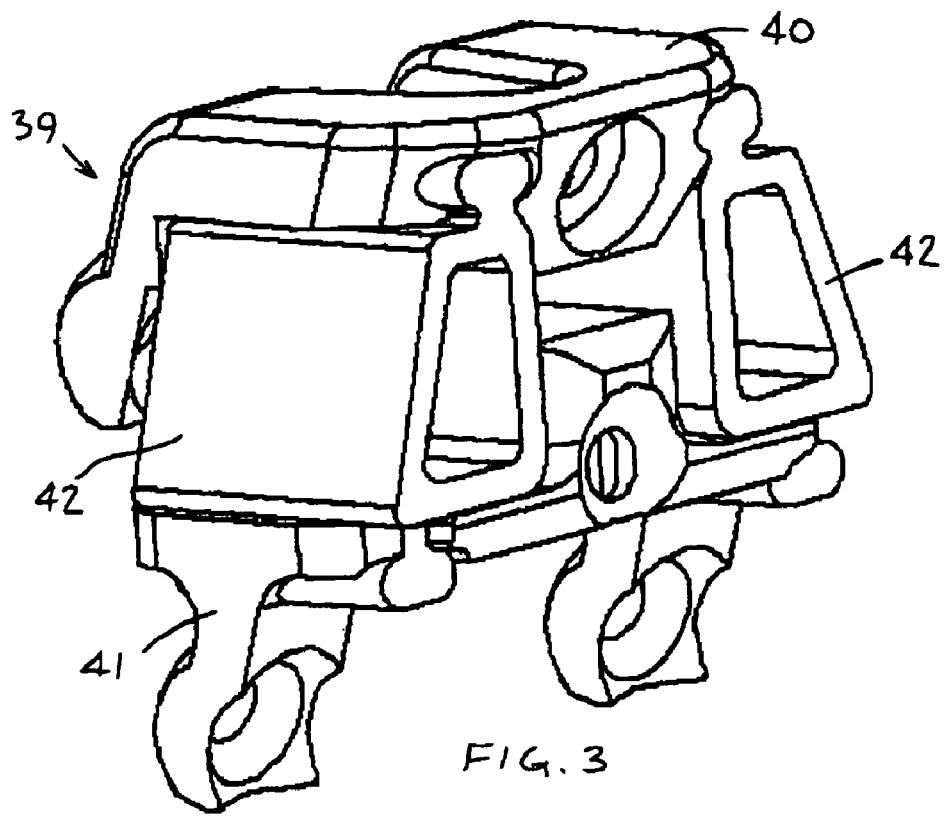
FIG. 3 is a simplified perspective illustration of an elastomeric spinal prosthesis, constructed and operative in accordance with yet another embodiment of the present invention, adapted for attachment to a posterior portion of the spine and to other vertebral structure, e.g., a facet or pedicle of the same vertebra.

Reference is now made to FIG. 3, which illustrates an elastomeric spinal prosthesis 39, constructed and operative in accordance with yet another embodiment of the present invention. Prosthesis 39 may be attached, for example, to the spinous process 118 and to other vertebral structure, e.g., a facet 126 or pedicle 114 or any posterior portion of the spine (see FIGS. 1A and 1B; not shown in FIG. 3).

Figure 6:
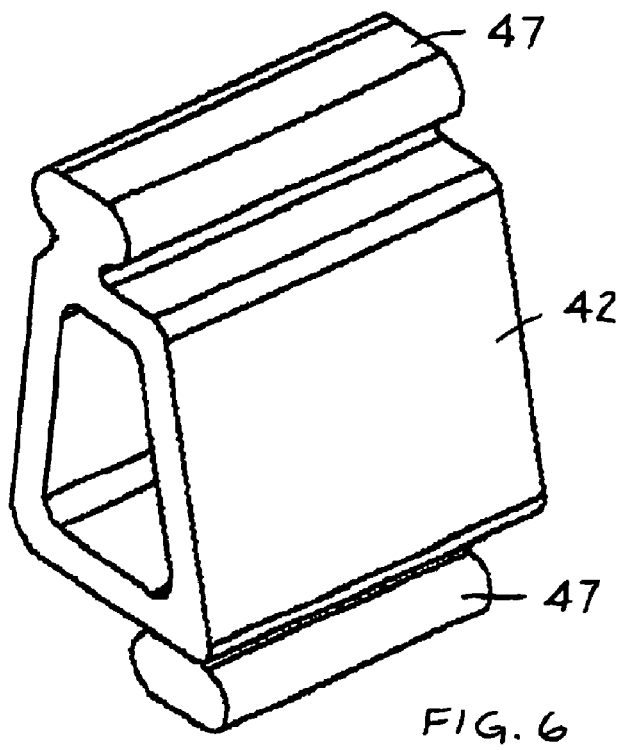
FIG. 6 is a perspective view of an elastomeric member of the prosthesis shown in FIG. 3.
Figure 7A:
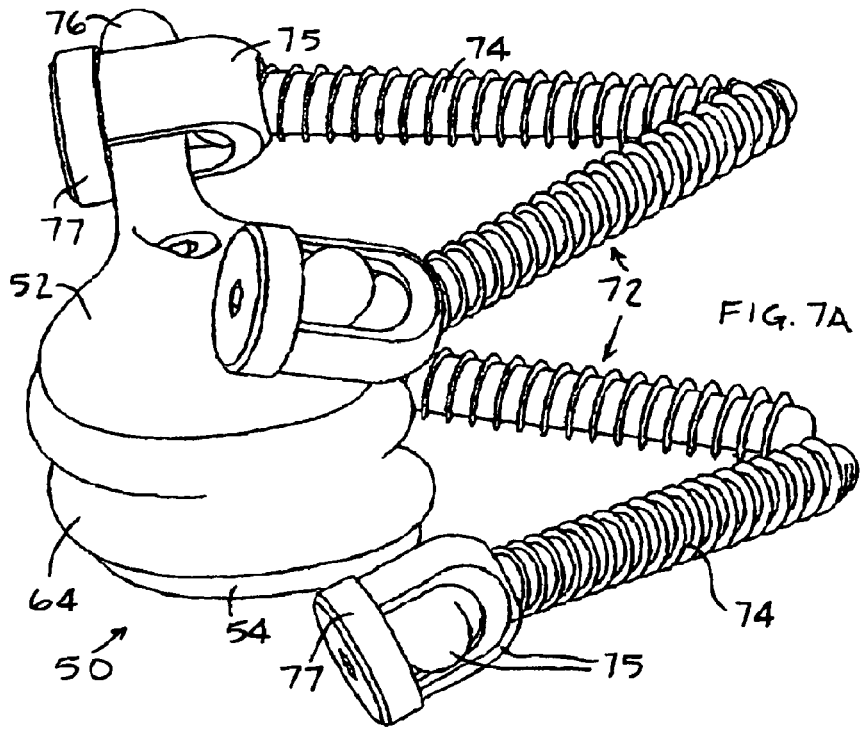
FIGS. 7A and 7B are simplified pictorial illustrations, from two different perspective views, of an elastomeric spinal prosthesis, constructed and operative in accordance with still another embodiment of the present invention.
Figure 7B:
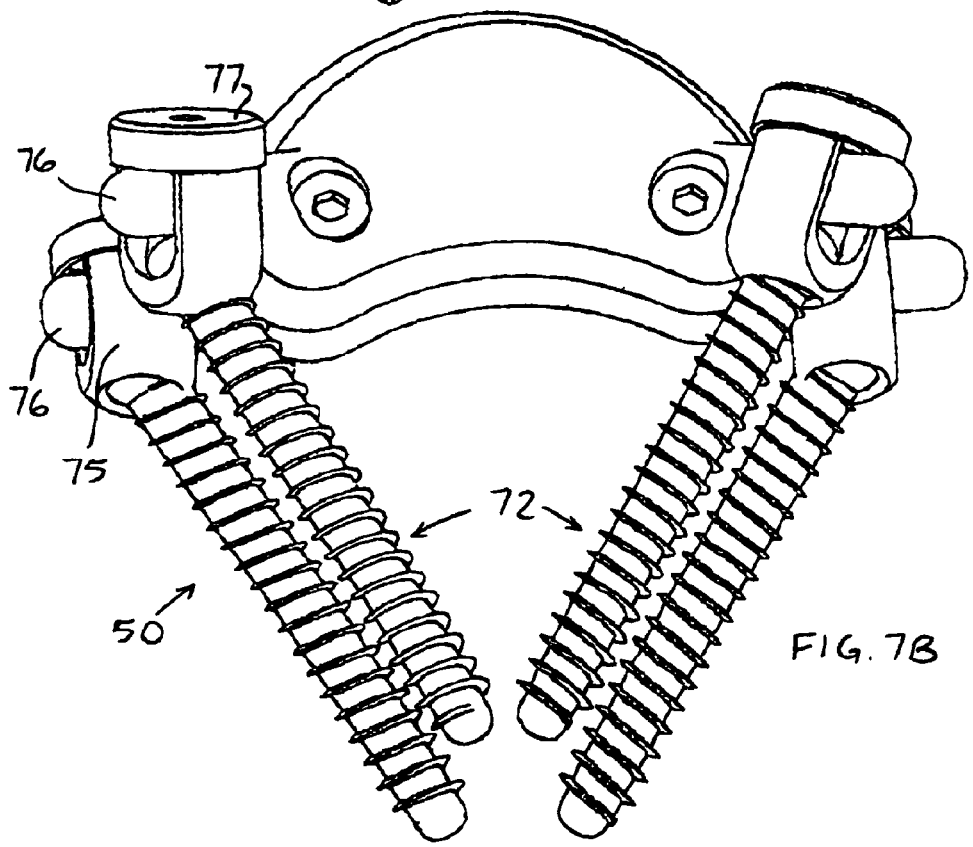

Prosthesis 39 may include an upper vertebral attachment member 40 attachable to the spinous process 118, facet 126 and/or pedicle 114, and a lower vertebral attachment member 41 attachable to another portion of the spine (not shown), such as an adjacent spinous process 118, facet 126 and/or pedicle 114. Attachment members 40 and 41 may be rigid or non-rigid, as above. One or more elastomeric members 42 (two are shown in this example; elastomeric members 42 also being referred to as a flexure assembly) may be placed between and may be integrally formed with or attached to upper and lower vertebral attachment members 40 and 41. Elastomeric member 42, shown clearly in FIG. 6, may be made from a compliant material as above.

In the embodiment of FIG. 3, but not necessarily, upper and lower vertebral attachment members 40 and 41 may be formed with one or more mounting holes adapted for a mechanical fastener (not shown) to pass through and into the portion of the spine. For example, any fastener or fasteners, such as but not limited to, screws, bolts, rivets, nails, tacks and nuts may pass through the mounting holes to firmly attach attachment members 40 and 41 to the spinous process 118.

Figure 4:
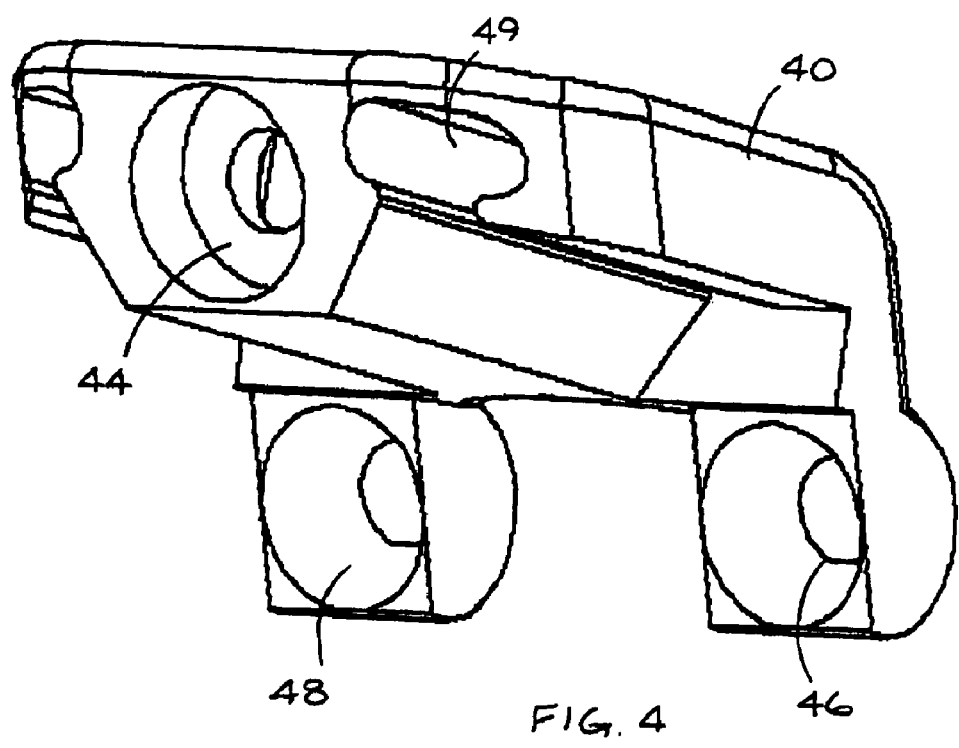
FIG. 4 is a perspective view of a superior attachment member of the prosthesis shown in FIG. 3.
Figure 5:
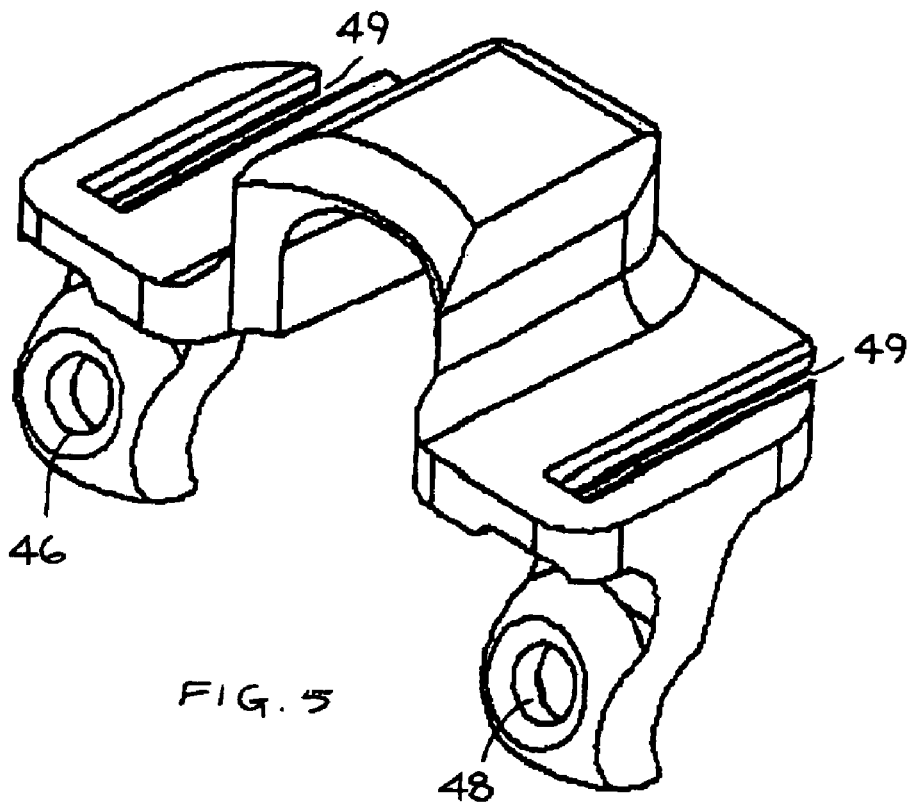
FIG. 5 is a perspective view of an inferior attachment member of the prosthesis shown in FIG. 3.

FIGS. 4 and 5 are posterior perspective views of non-limiting examples of upper and lower attachment members 40 and 41, respectively, as shown in FIG. 3. A mounting hole 44 is formed for attaching attachment member 40 to the posterior of one of the spinous processes 118, for example. Another mounting hole 46 in member 40 may be for fixation to the right facet 126 of the same vertebra and yet another mounting hole 48 may be for fixation to the left facet 126 of the same vertebra. The three-point fixation or attachment may provide a stable and more secure attachment of member 40 to the vertebra posteriorly with a minimum amount of invasiveness.

In the embodiment of FIG. 3, but not necessarily, elastomeric member may be attached to or integrally formed with upper and lower vertebral attachment members 40 and 41 by means of a tenon-and-mortise joint. The tenon-and-mortise joint may comprise tenons 47 (protrusions) that mate with mortises (grooves) 49. However, the invention is not limited to this type of joint or connection, and other types of joints, connections, fastenings, adhesive bonding and the like may also be used.

It is noted that the mounting holes may be placed and oriented in a multitude of manners. For example, in the embodiment of FIG. 1C, the mounting holes 24 do not pass through a plane that intersects elastomeric member 22. The mounting holes 24 are generally transverse to a longitudinal axis of elastomeric member 22. In contrast, in the embodiment of FIG. 3, the mounting hole 44 passes through a plane that intersects elastomeric member 42. The mounting holes 44, 46 and 48 are generally parallel to the longitudinal axis of elastomeric member 42. Other arrangements are also within the scope of the invention.

Reference is now made to FIGS. 7A, 7B, 8A and 8B, which illustrate an elastomeric spinal prosthesis 50, constructed and operative in accordance with still another embodiment of the present invention. Prosthesis 50 may be attached, for example, to the spinous process 118 and pedicles 114 (see FIGS. 1A and 1B; not shown in FIGS. 7A, 7B, 8A and 8B).

Prosthesis 50 may include an upper (superior) vertebral attachment member 52 and a lower (inferior) vertebral attachment member 54. The attachment members 52 and 54 may be attached to adjacent spinous processes 118, but as is described further hereinbelow, the prosthesis 50 may be attached to pedicles without having to attach the attachment members 52 and 54 to the spinous processes 118. Attachment members 52 and 54 may be rigid or non-rigid, formed of materials including, but not limited to, a biocompatible material such as a metal, e.g., stainless steel, titanium or titanium alloy, cobalt chromium alloys, plastics or other hard, rigid materials or any combination of the above.

A flexure assembly 56, comprising one or more flexing members (described below), may be placed between and may be integrally formed with or attached to upper and lower vertebral attachment members 52 and 54. Flexure assembly 56 may be attached to upper and lower vertebral attachment members 52 and 54 by means of locking members 58. Locking members 58 may include plate-like elements 59 secured to upper and lower vertebral attachment members 52 and 54 with mechanical fasteners 60, such as but not limited to, screws. Locking members 58 may further include lugs 61 extending generally perpendicularly from plate-like elements 59, around which stoppers 62 are securely engaged. Four such stoppers 62 are shown in the illustrated embodiment, however, the invention may be carried out with any number of such stoppers. A boot 64 may be placed at least partially or fully around inner portions of the attachment members 52 and 54, e.g., at least partially or fully around the locking members 58 and stoppers 62. The boot 64 may have any suitable shape or size, such as but not limited to, a ring, a stocking, an ellipsoid and other shapes. As seen clearly in FIGS. 8A and 8B, the boot 64 is sandwiched between upper and lower vertebral attachment members 52 and 54, and connected to locking members 58, such as but not necessarily, by means of inner ridges 65 of boot 64 fixedly engaging grooves 66 formed in plate-like elements 59 (as seen best in FIG. 8B). Thus, flexure assembly 56 comprises stoppers 62 and boot 64. The flexure assembly 56 may be constructed of a compliant, elastomeric material including, but not limited to, polyurethane containing materials, silicone containing materials, polyethylene based elastomers, hydrogels, and polypropylene containing materials. Alternatively, the flexure assembly 56 may be constructed of rigid materials, such as stainless steel, for example. In any case, boot 64 is made of a compliant material, such as but not limited to, an elastomer (e.g., polyurethane) or cloth (woven or non-woven synthetic or natural fibers).

Figure 8B:
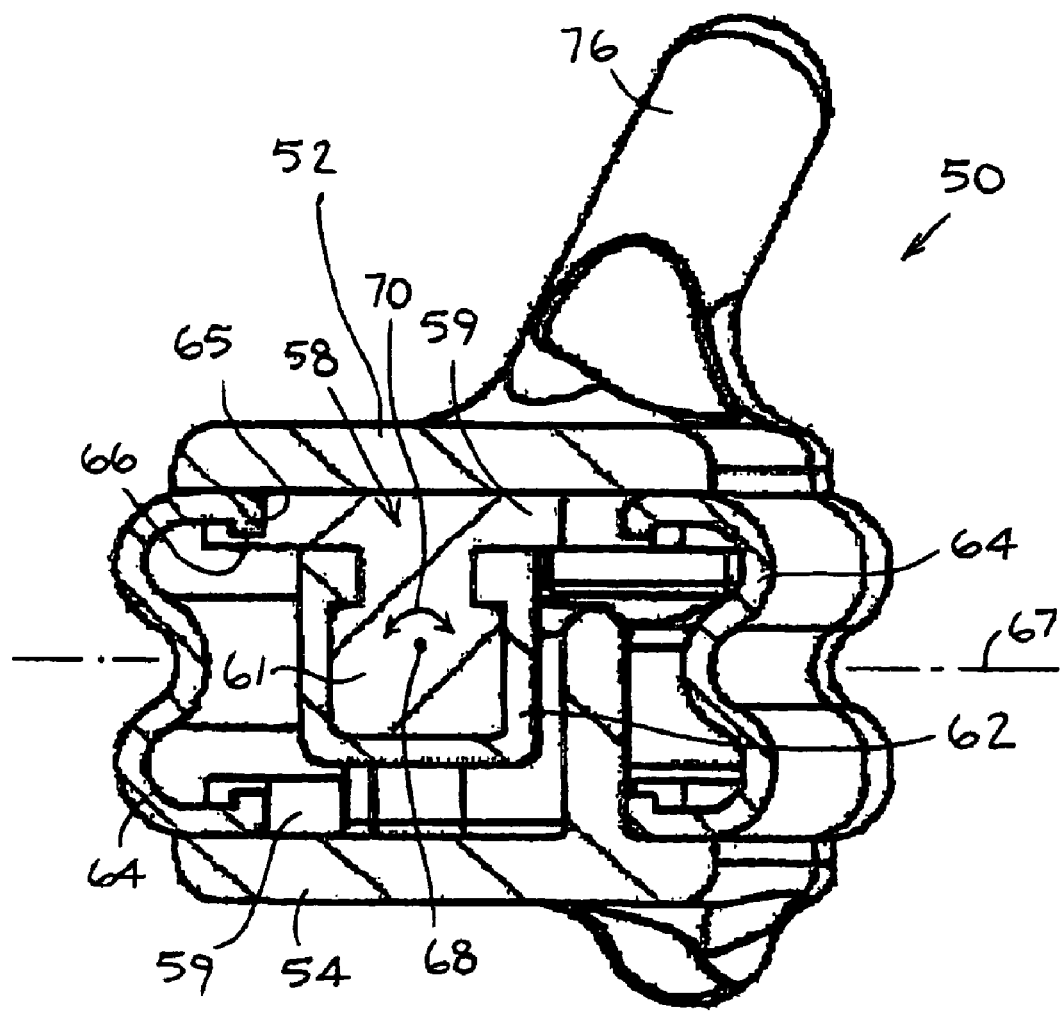

The flexure assembly 56 permits flexure of prosthesis 50 about two mutually orthogonal axes 67 and 68, as well as other directions for omnidirectional flexure in any degree of freedom. For example, as seen in FIG. 8A, prosthesis 50 can resiliently rotate about axis 67 in the direction of arrows 69. As seen in FIG. 8B, prosthesis 50 can resiliently rotate about axis 68 in the direction of arrows 70. The stoppers 62 (as well as boot 64 to some extent) may limit the flexure of flexure assembly 56 and thus limit the relative movement of the attachment members 52 and 54 with respect to one another.

Depending from prosthesis 50 are pedicle screws 72 (FIGS. 7A and 7B) for installing prosthesis 50 into the pedicles 114. The pedicle screws 72 may comprise, without limitation, polyaxial pedicle screws, e.g., made of titanium or titanium alloy, commercially available in many sizes and shapes from many manufacturers. It is noted that titanium is highly resistant to corrosion and fatigue, and is MRI compatible. The pedicle screw 72 may have a threaded shank 74 and a mobile, swivel head 75, whose ability to swivel may help avoid vertebral stress. The swivel heads 75 may be rotatably attached to rounded prongs 76 jutting from upper and lower vertebral attachment members 52 and 54, by means of lock nuts 77 that mate with heads 75.

In order to install prosthesis 50, a laminactomy may be performed, thereby creating a gap between the spinous processes 118, as mentioned hereinabove. The pedicle screws 72 may be screwed into the pedicles 114. The prosthesis 50 may be inserted in the gap between the spinous processes 118, with the rounded prongs 76 aligned with the heads 75 of the pedicle screws 72. The lock nuts 77 may then secure the prosthesis 50 to the pedicle screws 72. As mentioned before, the prosthesis 50 may thus be attached to the pedicles without having to attach the attachment members 52 and 54 to the spinous processes 118. Optionally, the attachment members 52 and 54 may also be attached to adjacent spinous processes 118 or other spinal structure by any convenient method. The outer surfaces of attachment members 52 and 54 may be coated with a material, such as but not limited to, Hydroxy-Appatite (H/A), which encourages bone growth into the outer surfaces thereof.

Figure 8C:
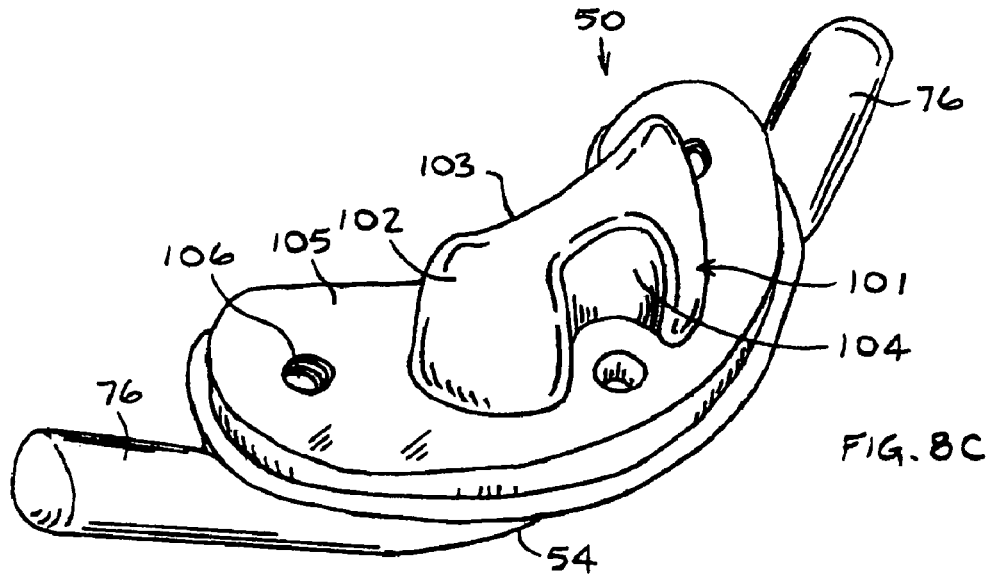
FIGS. 8C and 8D are simplified sectional illustrations of an alternative construction of a flexure assembly of the elastomeric spinal prosthesis of FIGS. 8A and 8B.
Figure 8D:
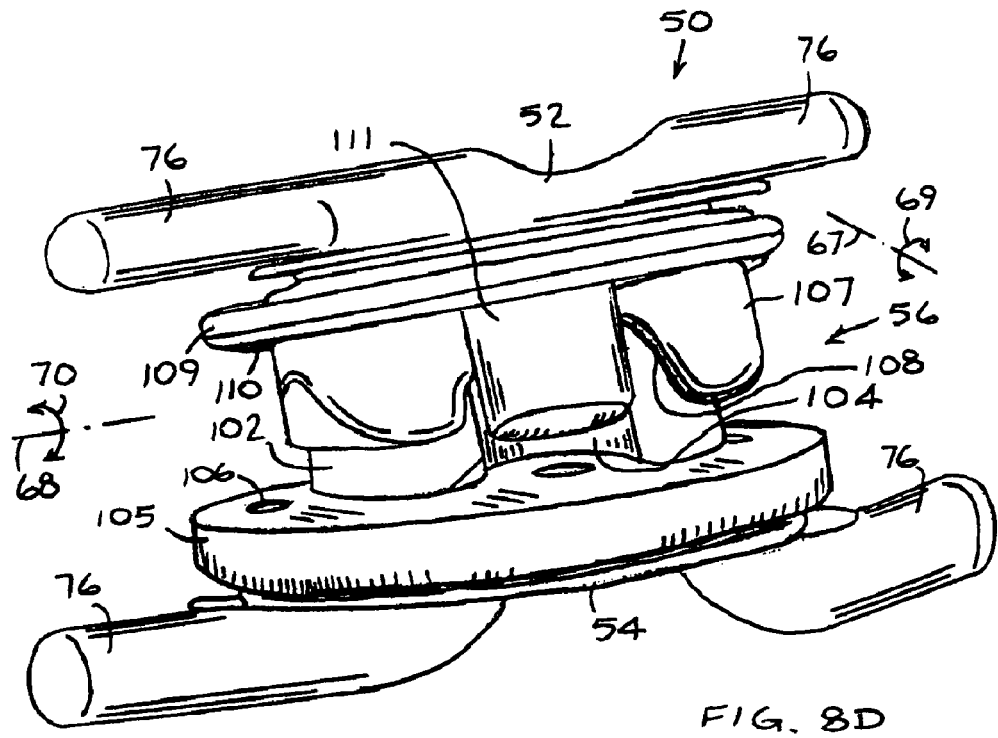

Reference is now made to FIGS. 8C and 8D, which illustrate an alternative construction of the flexure assembly 56 of the elastomeric spinal prosthesis 50. (The elastomeric boot 64 is omitted for clarity.) In this alternative construction, flexure assembly 56 may be constructed may include a two-part articulating assembly, constructed of a first joint member 101, which may have a convex outer contour 102 with a truncated face 103. A semi-circular cutout 104 may be gouged out of the convex outer contour 102. A plate 105 may secure the first joint member 101 to the lower attachment member 54, such as with screws (not shown) that pass through mounting holes 106.

The other part of the two-part articulating assembly of flexure assembly 56 may include a second joint member 107, which may have a concave outer contour 108 that corresponds to and glides over the convex outer contour of the first joint member 101. A plate 109 may secure the second joint member 107 to the upper attachment member 52, such as with screws (not shown) that pass through mounting holes 110. A stopper 111 may be provided, either as part of the second joint member 107 or as a separate part attached to the upper attachment member 52. The stopper 111 protrudes into the semi-circular cutout 104.

As similarly described above, this version of the flexure assembly 56 shown in FIGS. 8C and 8D permits flexure of prosthesis 50 about two mutually orthogonal axes 67 and 68 as well as other directions for omnidirectional flexure in any degree of freedom. For example, as seen in FIG. 8A, prosthesis 50 can resiliently rotate about axis 67 in the direction of arrows 69. As seen in FIG. 8B, prosthesis 50 can resiliently rotate about axis 68 in the direction of arrows 70. The stopper 111 may limit the flexure of flexure assembly 56 and thus limit the relative movement of the attachment members 52 and 54 with respect to one another.

It is noted that each of the spinal prostheses described hereinabove include a unitary body with at least three attachment points attachable to spinal structure. By "unitary body" it is meant that the spinal prosthesis may be attached to the spinal structure as one pre-assembled, contiguous assembly. The surgeon can simply hold the entire unitary body in place during attachment to the spinal structure. This is in contrast to known prostheses that must be attached to the spinal structure as at least two separate parts, which may or may not articulate with one another. With those prostheses, the surgeon must attach each part separately to some spinal structure and merely "hope" that the parts fit together properly after installment. The unitary construction of the present invention eliminates this problem and greatly facilitates installation of the prosthesis.

Even though embodiments were described above in which the attachment of attachment members was to either the spinous process alone or to the spinous process and to the facet or to the spinous process and to pedicle of the particular vertebra, it is feasible that any combination of the above embodiments will bring about similar results (such as stabilization of the spine, relief of pain, implantation of the prosthesis, etc.) and the above examples are just examples of attachment sites and not in any way meant to be limiting. For example a superior attachment member may be attached to a spinous process alone and the prosthesis's inferior attachment member may be attached to the adjacent vertebra's spinous process and to its pedicle or facet or even a combination of both. Similarly the prosthesis of this invention may be used in conjunction with an implant that is anterior to the spinal cord such as a total disc replacement.

Although the invention has been described in conjunction with specific embodiments thereof, many alternatives, modifications and variations are apparent to those skilled in the art. Accordingly, all such alternatives, modifications and variations fall within the spirit and scope of the following claims.

What is claimed is:

1. An article comprising:
    a spinal prosthesis comprising a first attachment member and a second attachment member, both adapted for attachment to adjacent spinal structure and both comprising elongate curved outer sides with rounded ends;
    a flexure assembly comprising one or more flexing members positioned between said first and second attachment members; and
    two pairs of elongate rods that extend from said attachment members adjacent said rounded ends.

2. The article according to claim 1, further comprising pedicle screws for attaching the first and second attachment members to spinal structure, wherein said elongate rods pass through heads of said pedicle screws.

\* \* \* \* \*